(12) United States Patent
Bert et al.

(10) Patent No.: US 8,217,373 B2
(45) Date of Patent: Jul. 10, 2012

(54) DETERMINATION OF A PLANNING VOLUME FOR IRRADIATION OF A BODY

(75) Inventors: Christoph Bert, Aschaffenburg (DE); Gerhard Kraft, Darmstadt (DE); Eike Rietzel, Weiterstadt (DE)

(73) Assignees: GSI Helmholtzzentrum fuer Schwerionenforschung GmbH, Darmstadt (DE); Siemens AG, Munich (DE)

( * ) Notice: Subject to any disclaimer, the term of this patent is extended or adjusted under 35 U.S.C. 154(b) by 370 days.

(21) Appl. No.: 12/532,601

(22) PCT Filed: Mar. 19, 2008

(86) PCT No.: PCT/EP2008/002246
§ 371 (c)(1),
(2), (4) Date: Nov. 18, 2009

(87) PCT Pub. No.: WO2008/116596
PCT Pub. Date: Oct. 2, 2008

(65) Prior Publication Data
US 2010/0074408 A1    Mar. 25, 2010

(30) Foreign Application Priority Data

Mar. 23, 2007  (DE) .......................... 10 2007 014 723
Mar. 26, 2007  (DE) .......................... 10 2007 014 394

(51) Int. Cl.
*A61N 5/10*    (2006.01)
*A61B 6/00*    (2006.01)
(52) U.S. Cl. .............. 250/492.3; 250/492.1; 250/396 R; 250/252.1; 378/4; 378/16; 378/62; 378/65; 382/130; 382/132; 600/411; 703/11

(58) Field of Classification Search .............. 250/492.1, 250/492.3, 396 R; 378/16, 62, 65; 382/130, 382/132; 600/411; 703/11
See application file for complete search history.

(56) References Cited

U.S. PATENT DOCUMENTS 4,123,654 A * 10/1978 Reiss et al. ...................... 378/87
4,427,890 A *  1/1984 Taumann .................... 250/385.1
(Continued)

FOREIGN PATENT DOCUMENTS

| GB | 2 371 462 A | 7/2002 |
| JP | 2006-043235 | 2/2006 |
| WO | WO 91/18552 A | 12/1991 |

(Continued)

OTHER PUBLICATIONS

Engelsman, Martijn et al.: "Impact of simple tissue inhomogeneity correction algorithms on conformal radiotherapy of lung tumours", *Radiotherapy & Oncology*, 60, 2001, pp. 299-309.
Chu, Millie et al.: "Robust optimization for intensity modulated radiation therapy treatment planning under uncertainty", *Phys. Med. Biol.*, 50 (2005), pp. 5463-5477.

*Primary Examiner* — David A Vanore
(74) *Attorney, Agent, or Firm* — Frommer Lawrence & Haug LLP; Ronald R Santucci

(57) ABSTRACT

A system for irradiating a predetermined target volume in a body with a particle beam is constructed to direct the particle beam at a multiplicity of target points in the body in succession, in order to produce at each of the target points a predetermined dose distribution. For the system there is determined a planning target volume by first determining, in a fictive homogeneous body, a target volume equivalent to the minimum target volume in the body. The equivalent target volume is extended by a safety margin, in order to determine the planning target volume.

24 Claims, 4 Drawing Sheets

U.S. PATENT DOCUMENTS

| | | | |
|---|---|---|---|
| 5,867,555 A * | 2/1999 | Popescu et al. | 378/16 |
| 6,501,828 B1 * | 12/2002 | Popescu | 378/150 |
| 6,792,066 B1 * | 9/2004 | Harder et al. | 378/4 |
| 6,845,141 B2 * | 1/2005 | Flohr et al. | 378/4 |
| 6,937,690 B2 * | 8/2005 | Bruder et al. | 378/15 |
| 7,342,398 B2 * | 3/2008 | Bielmeier et al. | 324/314 |
| 7,453,981 B2 * | 11/2008 | Baumann et al. | 378/62 |
| 7,482,605 B2 * | 1/2009 | Kraft et al. | 250/492.3 |
| 7,486,770 B2 * | 2/2009 | Baumann et al. | 378/62 |
| 7,539,336 B2 * | 5/2009 | Bohm et al. | 382/130 |
| 7,622,921 B2 * | 11/2009 | Fontius et al. | 324/307 |
| 7,650,023 B2 * | 1/2010 | Fischer et al. | 382/128 |
| 7,826,651 B2 * | 11/2010 | Bohm et al. | 382/130 |
| 7,920,675 B2 * | 4/2011 | Lomax et al. | 378/65 |
| 7,940,893 B2 * | 5/2011 | Krauss | 378/98.9 |
| 7,960,710 B2 * | 6/2011 | Kruip et al. | 250/492.3 |
| 8,017,906 B2 * | 9/2011 | Nelson et al. | 250/252.1 |
| 8,041,096 B2 * | 10/2011 | Bernhardt et al. | 382/132 |
| 2004/0242991 A1 | 12/2004 | Frohlich et al. | |
| 2005/0201516 A1 | 9/2005 | Ruchala et al. | |
| 2007/0034812 A1 | 2/2007 | Ma et al. | |
| 2009/0234219 A1 * | 9/2009 | Kruip | 600/411 |
| 2009/0234626 A1 * | 9/2009 | Yu et al. | 703/11 |
| 2010/0013418 A1 * | 1/2010 | Kruip et al. | 315/501 |
| 2010/0108903 A1 * | 5/2010 | Bert et al. | 250/396 R |
| 2010/0327188 A1 * | 12/2010 | Bert et al. | 250/492.3 |
| 2011/0272600 A1 * | 11/2011 | Bert et al. | 250/492.1 |
| 2011/0303857 A1 * | 12/2011 | Bert et al. | 250/492.1 |

FOREIGN PATENT DOCUMENTS

| | | |
|---|---|---|
| WO | WO 03/76003 A | 9/2003 |
| WO | WO 03/092813 | 11/2003 |

* cited by examiner

DETERMINATION OF A PLANNING VOLUME FOR IRRADIATION OF A BODY

This application is a 371 of PCT/EP2008/002246 filed on Mar. 19, 2008, published on Oct. 2, 2008 under publication number WO 2008/116596 A which claims priority benefits from German Patent Application Number 10 2007 014 723.8 filed Mar. 23, 2007 and German Patent Application Number 10 2007 014 394.1 filed Mar. 26, 2007, the disclosures of both are incorporated herein by reference.

The present invention relates to a method and apparatus for determination of a planning volume for a particle therapy system for irradiation of an at least in some instances moving predetermined target volume in a raster scanning method or in a spot scanning method or in a continuous scanning method or in some other scanning method.

Tumour therapy using particle beams, especially protons, α particles and carbon nuclei, is increasing in importance. In that context, the raster scanning method has a number of advantages over other methods. In this method, a three-dimensional raster is placed over the tumour volume. The particle beam is deflected by deflecting magnets in two directions perpendicular to one another (the x and the y directions). By actively varying the particle energy, the position of the Bragg peak, in which the largest portion of the dose is deposited, is set at differing tissue depths (z direction).

Computed tomography devices, nuclear spin tomography devices and other imaging apparatus have limited spatial resolution. Between the imaging of a tumour in a body and the irradiation with a particle beam there is a time interval in which the position and size of the tumour may change. The position and size of the tumour in the patient can also change during fractionated irradiation, which may extend over days or weeks. Furthermore, the positioning of the patient can be different from one fraction to another in the case of protracted irradiation (irradiation programme comprising a plurality of individual irradiations in each of which only a fraction or proportion of the total dose is applied). Consequently both the tumour and also the patient as a whole are located in slightly different positions. A number of organs that are of relevance in tumour therapy are located in the vicinity of the lungs and are therefore also caused to move with the movements of the patient's breathing.

For these and other reasons, the position and size of a tumour, or also any other target region, in a patient's body are only ever known with a certain inaccuracy or uncertainty. An underdose at the edge of a tumour jeopardises therapeutic success.

A problem of the present invention is to determine a planning volume for a raster scanning method so that complete irradiation of a target region is accomplished even in the case of positional inexactitudes.

That problem is solved by a method according to claim 1 and by an apparatus according to claim 15.

Preferred developments of the present invention are defined in the dependent claims.

The present invention is based on the idea that there is first determined, in a fictive homogeneous body, a target volume equivalent to a minimum target volume in a body, for example a volume for which therapy has been justified. A real body is always non-homogeneous. The interaction of the particle beam with the body, especially the loss of energy of the particle beam in the body, is therefore location-dependent. Extreme examples of structures in which a particle beam loses energy especially rapidly or especially slowly are, respectively, bones and the lungs or other cavities. The fictive homogeneous body consists, for example, of water, in which case it is referred to as a water equivalent.

In a further step, the equivalent target volume is extended by a safety margin. The extended equivalent target volume is the planning target volume. The width and/or thickness of the safety margin is matched to the accuracy with which the position of the minimum target volume is known, and/or to the accuracy with which the composition of the body is known, and/or to the accuracy with which the patient's position is known, and/or to the extent of possible changes before or during the irradiation, and/or to the accuracy with which the location (co-ordinates perpendicular to the beam direction) and/or the accuracy with which the energy of the particle beam is/are known, and/or to the accuracy with which the beam focus and/or beam cross-section is/are known, and/or to the accuracy with which the conversion to the equivalent target volume is known or is carried out. Possible changes are, especially, growth or movement of the minimum target volume in the body or movement of the body together with the minimum target volume. The width and/or thickness of the safety margin can be the same in each spatial direction or different in each spatial direction and, for example, larger in the main movement direction than in other directions.

Empirical values such as those known from clinical practice can enter into the dimensioning of the safety margin and include, for example, the accuracy with which the position of the patient is known, or typical movements of the minimum target volume or of other regions within the patient that are located in front of the minimum target volume in the beam direction. If the amplitude or speed of a movement of the minimum target volume due to breathing or some other reason is known, it can enter into the dimensioning of the safety margin. In the case of a movement of the minimum target volume, several different positions of the minimum target volume can also be used as the basis for the dimensioning of the safety margin or for the formation of the planning target volume. Those several different positions can be determined using, for example, 4DCT (time-resolved computed tomography) or other time-resolved imaging methods. An alternative example is the evaluation of several CT recordings or other recordings without defined time correlation (for example, made on different days). From such recordings that have not been correlated in defined manner, statistical information is then obtained relating to the variability of the location and of the extent of the minimum target volume within the patient and relating to the variability of other regions (for example, organs) within the patient that are located in front of the minimum target volume in the beam direction. For each known position or at least for each of the extreme positions of the minimum target volume there is determined an equivalent target volume in the fictive homogeneous body. The planning target volume is then determined so that it includes all the equivalent target volumes. In particular, the planning target volume can be determined as the union of sets of all the equivalent target volumes. In the case of two equivalent target volumes, the safety margin is the difference between the planning target volume and one of the equivalent target volumes. In addition, the planning volume can be extended by a further safety margin around the union of sets of the equivalent target volumes.

The extents of the safety margin in all three spatial directions can be either identical or different from one another, and either the same at all locations or location-dependent. In a simple case, the safety margin has, independently of location, a width and/or thickness which in all spatial directions is the same or has different values. The target volume is calculated, for example, by convolution of the equivalent target volume or of the union of sets of the equivalent target volumes using a convolution kernel. The convolution kernel describes the dimensions of the safety margin.

The invention will be explained in greater detail hereinbelow by way of example with reference to the accompanying Figures, in which.

Figure 1:
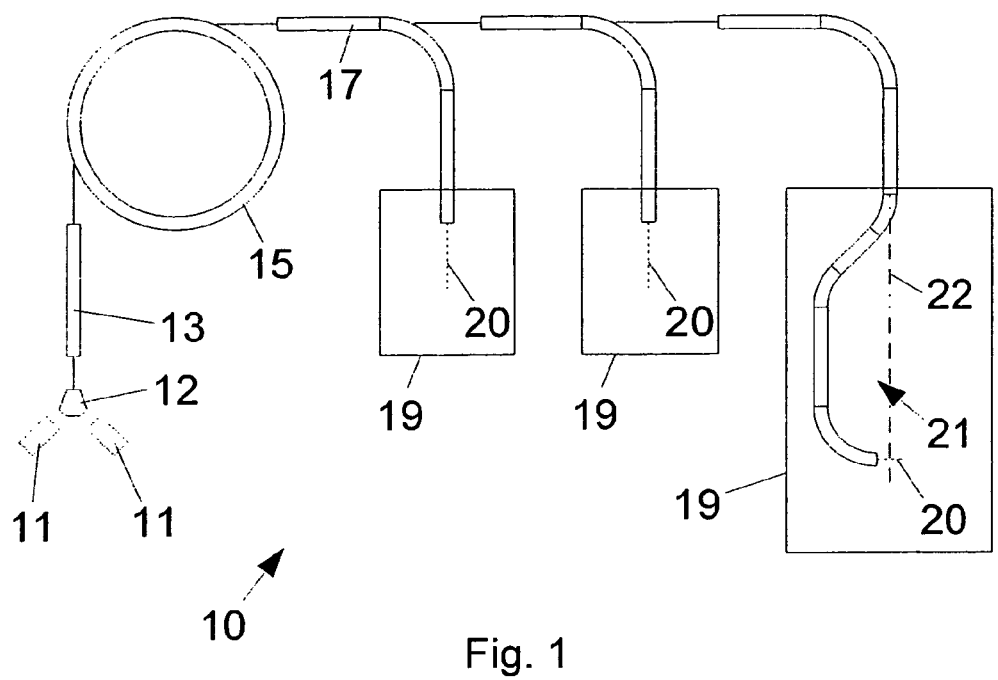
FIG. 1 shows, in diagrammatic form, a particle therapy system.

FIG. 1 shows, in diagrammatic form, an overview of the structure of a particle therapy system 10. In a particle therapy system 10, irradiation, especially of tissue with tumour disease, is carried out with a particle beam 20. The particles used are, in the main, ions such as, for example, protons, pions, helium ions, carbon ions or other ion types.

Usually, such particles are produced in a particle source 11. If, as shown in FIG. 1, there are provided two particle sources 11, which produce two different ion types, it is possible to switch over between those two ion types within a short time interval. For this purpose there is used, for example, a switching magnet 12 arranged between, on the one hand, the ion sources 11 and, on the other hand, a pre-accelerator 13.

Examples that may be mentioned of two different ion types which can be alternatively used in a particle therapy system are helium ions ($^3$He or $^4$He) and carbon ions. These differ in the biological effect of their beams and are suitable for different types of tumours. $^4$He and $^{12}$C both have, in the fully ionised state, the same A/Q ratio between the mass number A and charge Q. They can therefore be accelerated in the same acceleration system without major adaptation.

The ions produced by the or by one of the ion source(s) 11 and, where applicable, selected using the switching magnet 12 are accelerated to a first energy level in the pre-accelerator 13. The pre-accelerator 13 is, for example a linear accelerator (LINAC for: "LINear ACcelerator"). The particles are then fed into an accelerator 15, for example a synchrotron or cyclotron. In the accelerator 15 they are accelerated to high energies as are required for the purpose of irradiation. After the particles leave the accelerator 15, a high-energy beam transport system 17 guides the particle beam 20 to one or more irradiation rooms 19. In an irradiation room 19, the accelerated particles are directed at a body to be irradiated. Depending on the particular arrangement, this is carried out from a fixed direction (in so-called "fixed beam" rooms) or, however, by means of a rotatable gantry 21 which can be moved about an axis 22, from different directions.

The basic structure, shown by FIG. 1, of a particle therapy system 10 is typical of many particle therapy systems but can also differ therefrom. The exemplary embodiments described hereinbelow can be used both in conjunction with the particle therapy system shown by FIG. 1 and also with other particle therapy systems.

FIGS. 2 to 17 show, in diagrammatic form, sections through bodies to be irradiated or through target volumes. The sections lie parallel to the direction of a particle beam. Three-dimensional rasters of regions or target points 30, each of which is shown in the Figures as a square, are placed over the bodies to be irradiated and over the target volumes. In each case, one layer of the three-dimensional raster of regions or target points 30 is shown. In the case of FIGS. 2, 7, 8, 12 and 13, the squares shown are not target points but merely represent the raster in which the real body is detected by an imaging method. In the case of the equivalent homogeneous structures, which are shown in FIGS. 3 to 5, 9 to 11 and 14 to 17, each square is a target point.

In FIGS. 2, 7, 8, 12 and 13, simple diagonal hatching with two different spacings between the lines differentiates regions or target points having two different densities or physical properties. The loss of energy of a particle in a region with closely spaced hatching is twice the loss of energy in a region with widely spaced hatching. Of course, other and substantially finer differentiations of energy loss are also possible. The loss of energy in a region can be determined from the local densities of CT recordings, for example using the Hounsfield Look-Up Table (HLUT). In each case, the bodies and target volumes shown are to be irradiated by a horizontal particle beam coming from the left.

Figure 2:
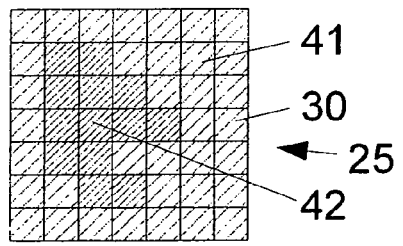
FIG. 2 shows, in diagrammatic form, a section through a minimum target volume to be irradiated.

FIG. 2 shows a minimum target volume 25 to be irradiated, in its desired location or position as expected on the basis of imaging carried out prior to the irradiation. In the section shown, it has the shape of a square. In respect of interaction with the particle beam provided for the irradiation, the minimum target volume 25 is non-homogeneous. In regions 42 the particles of the beam lose twice as much energy over a given path as they lose in regions 41 over a path of the same length. The loss of energy is substantially governed by the density of the material passed through. As an approximation, therefore, the regions 41 can be described as regions of low density and the regions 42 as regions of high density. Examples of regions of low density are muscles, organs and other soft tissue consisting largely of water; examples of regions of high density and high energy loss are bones.

Figure 3:
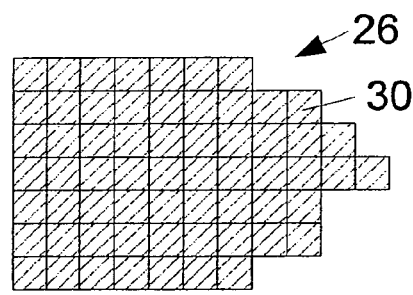
FIG. 3 shows, in diagrammatic form, a section through an equivalent homogeneous target volume.

FIG. 3 shows a fictive equivalent homogeneous target volume 26, which in respect of its interaction with the particle beam provided for the irradiation is equivalent to the minimum target volume 25 shown hereinbefore by FIG. 2. By way of explanation of the equivalence, a particle beam is considered, entering the target volume horizontally from the left and, in the process, passing through a line of the squares shown in FIGS. 2 and 3. In a particular line of FIG. 3, the particle beam must, in order to reach the right-hand edge of the equivalent target volume 26 exactly, have the same initial particle energy as in the corresponding line of FIG. 2 in order to reach the right-hand edge of the minimum target volume 25 exactly. The equivalent homogeneous target volume 26 consists, for example, of water (water equivalent) or homogeneously of some other material. This material is, for example, so selected that the interactions of the particle beam with the material are similar to those with the real body to be irradiated. Isoenergy layers, that is to say layers in which particles of a particular initial particle energy are stopped, are flat in the equivalent homogeneous target volume 26 shown in FIG. 3.

Figure 4:
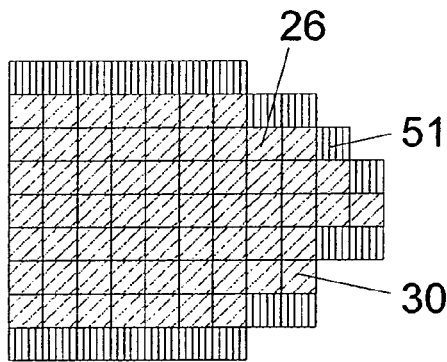
FIG. 4 shows, in diagrammatic form, a section through an equivalent homogeneous target volume having a lateral safety margin.

FIG. 4 shows the equivalent homogeneous target volume 26 already shown in FIG. 3, together with a lateral safety margin 51. The lateral safety margin 51 is formed by laterally extending each isoenergy layer of the equivalent homogeneous target volume 26. This lateral safety margin 51 ensures that, even in the event of a discrepancy between the actual position or location of the minimum target volume in the co-ordinate system of the irradiation system and the expected location in a transverse direction to the beam (more precisely: parallel to an isoenergy layer), the minimum target volume 25 will be irradiated completely.

Figure 5:
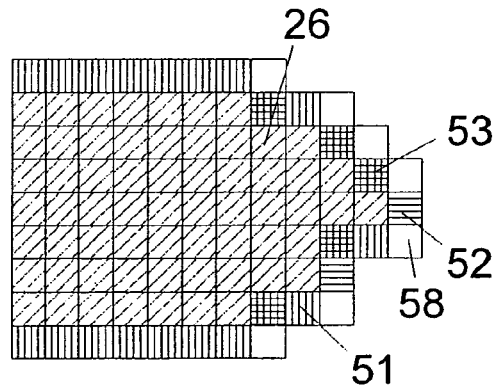
FIG. 5 shows, in diagrammatic form, a section through an equivalent homogeneous target volume having a safety margin.

FIG. 5 shows the equivalent homogeneous target volume 26 already shown in FIGS. 3 and 4, together with a safety margin which includes the lateral safety margin shown hereinbefore by FIG. 4 and a longitudinal safety margin 52. The longitudinal safety margin is formed by lengthening each row of target points located parallel to the beam direction. The longitudinal safety margin has the effect that, even in the event of a discrepancy between the actual position or location of the minimum target volume in the co-ordinate system of the irradiation system and the expected location in a direction parallel to the beam, the minimum target volume will, with sufficient probability, be irradiated completely. The longitudinal safety margin has the effect that, even in the event of a discrepancy between the density in the entry channel or, that is, in regions located in front of the minimum target volume in the beam direction and the density that is expected there, the minimum target volume will, with sufficient probability, be irradiated completely. There are target points 51 which are located only in the lateral safety margin, target points 52 which are located only in the longitudinal safety margin and target points 53 which are located both in the lateral and also in the longitudinal safety margin.

FIG. 5 furthermore shows target points 58 in an extended safety margin. This takes into account a discrepancy between the actual position or location of the minimum target volume in the co-ordinate system of the irradiation system and the expected location at the same time both in the direction parallel to the isoenergy layers and also in the direction parallel to the particle beam.

Figure 6:
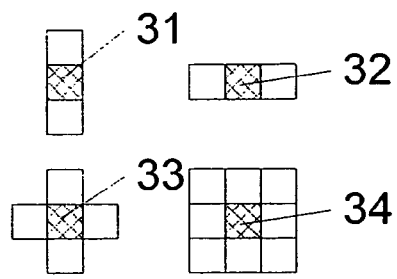
FIG. 6 shows, in diagrammatic form, convolution kernels.

FIG. 6 shows a series of convolution kernels 31, 32, 33, 34 for determination of the safety margin by convolution of the equivalent target volume using a convolution kernel. In each case, the middle cross-hatched area represents the reference point. A first convolution kernel 31 generates only a lateral safety margin, as is shown hereinbefore by FIG. 4. A second convolution kernel 32 generates only a longitudinal safety margin. When applied to the equivalent target volume 26 shown hereinbefore by FIG. 3 there is formed a safety margin which, in addition to the target points 52 and 53 shown hereinbefore by FIG. 5, also has target points at the left-hand edge of the equivalent target volume 26 which are not shown in FIG. 5. A third convolution kernel 33 generates a lateral and longitudinal safety margin. When applied to the equivalent target volume 26 shown hereinbefore by FIG. 3 there is formed a safety margin which, in addition to the target points 51, 52 and 53 shown hereinbefore by FIG. 5, also has target points at the left-hand edge of the equivalent target volume 26, which are not shown in FIG. 5. A fourth convolution kernel 34 generates an extended safety margin. When applied to the equivalent target volume 26 shown hereinbefore by FIG. 3 there is formed a safety margin which, in addition to the target points 51, 52, 53 and 58 shown hereinbefore by FIG. 5, also has target points at the left-hand edge of the equivalent target volume 26 which are not shown in FIG. 5.

Figure 7:
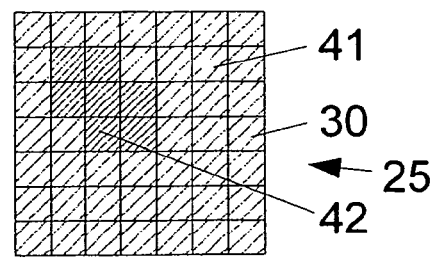
FIG. 7 shows, in diagrammatic form, a section through a minimum target volume to be irradiated, in a first state.
Figure 8:
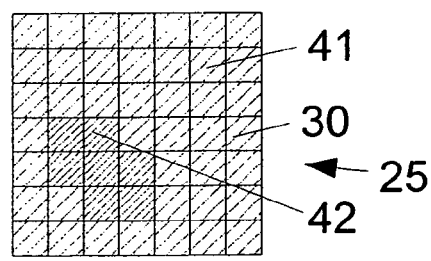
FIG. 8 shows, in diagrammatic form, a section through the minimum target volume to be irradiated, in a second state.

FIGS. 7 and 8 show a minimum target volume 25 to be irradiated which has non-homogeneity (regions 41 of low energy loss and regions 42 of high energy loss), in two different movement states. These two movement states can be detected, for example, using 4DCT (time-resolved computed tomography) or some other time-resolved imaging method, for example by means of nuclear spin resonance tomography (NMR), positron emission tomography (PET) etc. Alternatively, possible movement states are determined from a plurality of CT, NMR, PET or other images of the body that have not been correlated in time-defined manner and that provide statistical information relating to the variability of the body. In the case of a statistical position change (for example, from one day to another) or an oscillating movement, as is caused, for example, by breathing, the movement states shown in FIGS. 7 and 8 are, for example, the extreme states, between which the movement takes place. In the case of a movement of relatively large amplitude (more than one or two raster points) further movement states can be taken into account in addition thereto.

Figure 9:
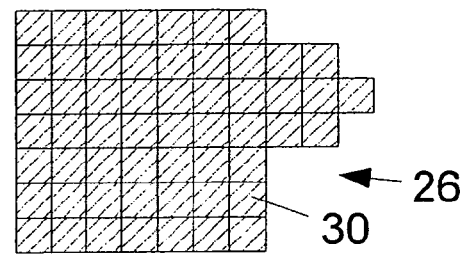
FIG. 9 shows, in diagrammatic form, a section through an equivalent homogeneous target volume.
Figure 10:
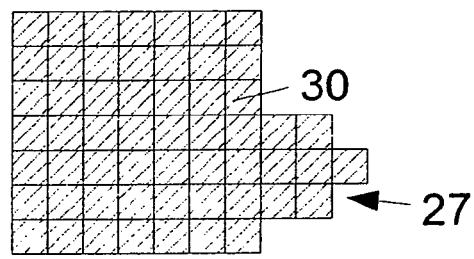
FIG. 10 shows, in diagrammatic form, a section through a further equivalent homogeneous target volume.

FIGS. 9 and 10 show, in diagrammatic form, sections through equivalent homogeneous target volumes 26, 27. These are equivalent, in the sense explained hereinbefore in the context of FIG. 3, to the minimum target volume 25 in the movement states shown in FIGS. 7 and 8, respectively.

Figure 11:
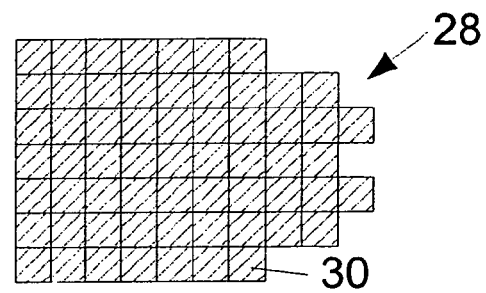
FIG. 11 shows, in diagrammatic form, a section through a union of sets of equivalent homogeneous target volumes.

FIG. 11 shows the union of sets 28 of the equivalent homogeneous target volumes 26, 27 shown in FIGS. 9 and 10. This represents a suitable planning target volume for the moving minimum target volume 25 shown in FIGS. 7 and 8. The difference between the planning target volume and the equivalent homogeneous target volume 26 shown in FIG. 9 represents a safety margin relative to the equivalent homogeneous target volume 27 shown in FIG. 10, and the difference between the planning target volume and the equivalent homogeneous target volume 27 shown in FIG. 10 represents a safety margin relative to the equivalent homogeneous target volume 26 shown in FIG. 9. The union of sets 28 can be additionally extended by a safety margin as has been shown hereinbefore by FIGS. 4 and 5.

Figure 12:
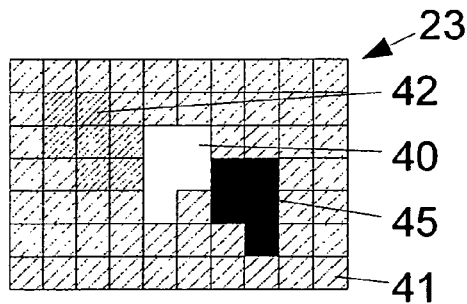
FIG. 12 shows, in diagrammatic form, a section through a body having a minimum target volume to be irradiated, in a first state.
Figure 13:
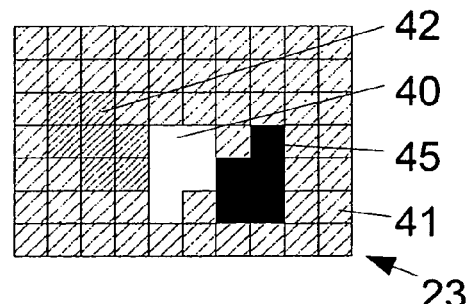
FIG. 13 shows, in diagrammatic form, a section through the body having the minimum target volume to be irradiated, in a second state.

In the examples shown hereinbefore by FIGS. 2 to 11, only the minimum target volume has been shown which has non-homogeneities and an internal movement. In contrast thereto, each of FIGS. 12 and 13 show a body 23 having non-homogeneities (regions 41, 42 of unitary and double energy loss, respectively) and a minimum target volume 45, which however occupies only a part of the body 23. The body 23 furthermore has a non-homogeneity in the entry channel or, that is, in regions located in front of the minimum target volume 45 in the beam direction. This non-homogeneity is, by way of example, shown as a cavity 40 in which a particle beam undergoes (almost) no loss of energy. Also, the minimum target volume 45 can itself have non-homogeneities, which for the sake of simplicity, however, are not shown in FIGS. 12 and 13.

FIGS. 12 and 13 show the body 23 again in two different movement states. In these two movement states, for example, both the locations of the non-homogeneities 41, 42 and also the location and spatial form of the minimum target volume are different. It is likewise possible, for example, for only the locations or only the spatial forms of the non-homogeneities 41, 42 or the extent of the non-homogeneity (for example, differences in density) or only the location or spatial form of the minimum target volume 45 to vary.

Figure 14:
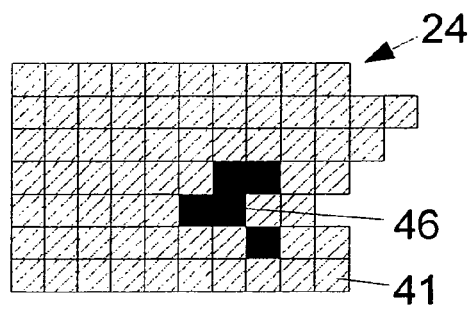
FIG. 14 shows, in diagrammatic form, a section through a homogeneous body equivalent to the body in the first state.
Figure 15:
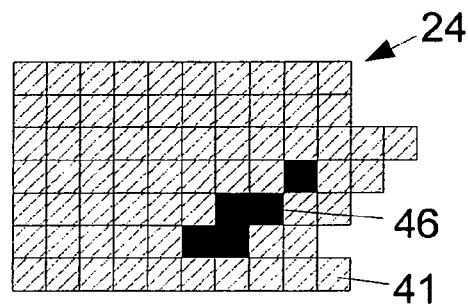
FIG. 15 shows, in diagrammatic form, a section through a homogeneous body equivalent to the body in the second state.

FIGS. 14 and 15 show, in diagrammatic form, sections through equivalent homogeneous bodies 24. These are equivalent, in the sense explained hereinbefore in the context of FIG. 3, to the body 23 in the movement state shown in FIG. 12 and to the body 23 in the movement state shown in FIG. 13, respectively. The equivalent homogeneous bodies 24 contain equivalent target volumes 46, which are equivalent to the minimum target volume 45 shown in FIGS. 12 and 13 in the corresponding movement state. It will be seen that the form of the equivalent target volume 46 in the two movement states differs from the form of the minimum target volume 45 shown in FIGS. 12 and 13. This is caused by the non-homogeneities 40, 42 located in front of the minimum target volume 45 in the beam direction.

Figure 16:
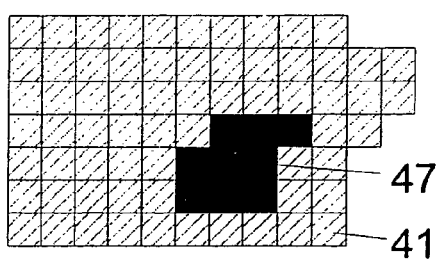
FIG. 16 shows, in diagrammatic form, a section through an equivalent homogeneous body including a composite equivalent target volume.

FIG. 16 shows the union of sets of the equivalent homogeneous body shown in FIGS. 14 and 15 with the union of sets 47 of the equivalent target volumes 46 shown in the same Figures. The union of sets represents a suitable planning target volume for the minimum target volume shown in FIGS. 12 and 13 in the moving body. The difference between the union of sets 47 and the equivalent homogeneous target volume 46 shown in FIG. 14 represents a safety margin relative to the equivalent homogeneous target volume 46 shown in FIG. 15, and the difference between the union of sets 47 and the equivalent homogeneous target volume 46 shown in FIG. 15 represents a safety margin relative to the equivalent homogeneous target volume 46 shown in FIG. 14.

Figure 17:
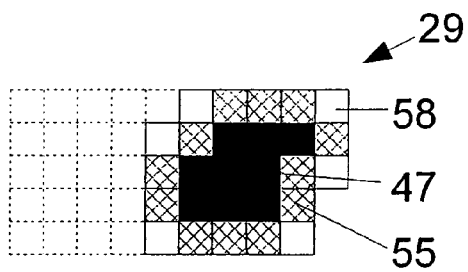
FIG. 17 shows, in diagrammatic form, a section through a planning target volume.

FIG. 17 shows, in isolation, just the planning target volume 29 formed from the union of sets 47. Surrounding regions of the body either are not shown or are shown by broken lines. The union of sets can additionally be extended by a safety margin 55, 58 as shown hereinbefore with reference to FIGS. 4 and 5. Target points 55 are located in the lateral safety margin and/or in the longitudinal safety margin; target points 58 form the extended safety margin as has been shown hereinbefore by FIG. 5. The planning target volume obtained in that manner is transferred, for example in the form of a data set, to a device which generates from the planning target volume a data set containing the locations (co-ordinates perpendicular to the beam direction), particle energies, beam cross-sections and particle counts for all the target points. From that data set, control parameters are determined in the same device or in a further device. The control parameters are transferred to a control device of the irradiation system 11 shown hereinbefore by FIG. 1.

The minimum target volume and the planning target volume have been shown hereinbefore by FIGS. 2 to 17 always in a three-dimensional raster or two-dimensional section thereof. This raster can, in contrast to the illustration in FIGS. 2 to 17, have periods that are different in the three spatial directions, that is to say can be non-cubic, and/or have different numbers of grid points in different spatial directions or as a whole and/or have different numbers of raster points in parallel planes. Furthermore, a hexagonal or also any other desired raster is possible.

The above-described determination of a planning target volume can be used for any irradiation wherein a particle beam is directed at a multiplicity of target points in succession in a continuous or non-continuous process. For example, the described measures can be used for a spot scanning method, wherein the particle beam remains at each target point for a predetermined time and/or deposits a predetermined number of particles and is switched off while deflecting magnets etc. are set for the next target point. The described measures can furthermore be used for a raster scanning method, wherein the particle beam remains at each target point for a predetermined period of time and/or deposits a predetermined number of particles but is not, or not always, switched off between the target points.

The above-described determination of a planning target volume is furthermore also suitable for a continuous scanning method. In a continuous scanning method, the target points form continuous lines, that is to say they form continuous (or quasi-continuous) sets, the number of which is countably infinite. In a continuous scanning method, the particle beam is continuously deflected at least within a line or row within an isoenergy layer and passes over the target points without remaining for a time at individual locations.

Figure 18:
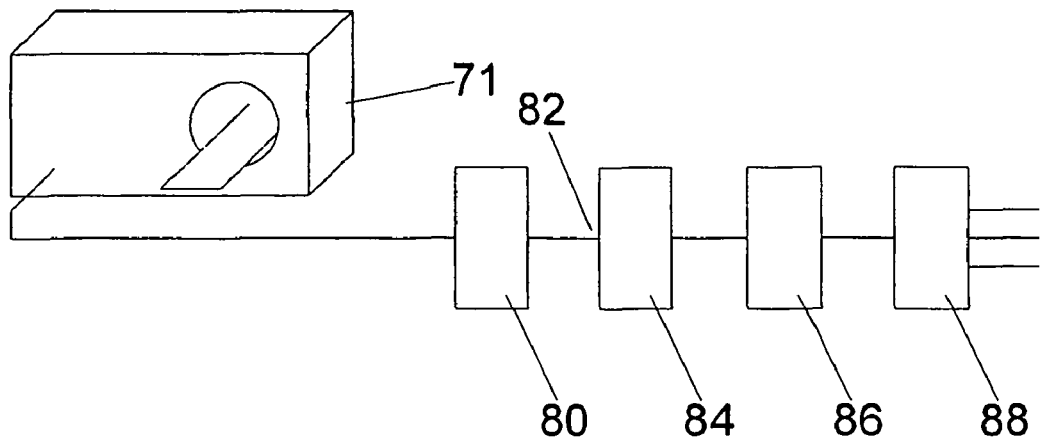
FIG. 18 shows, in diagrammatic form, an apparatus for the determination of a planning target volume for a particle therapy system.

FIG. 18 shows, in diagrammatic form, an apparatus for determination of a control parameter of a system for irradiating a predetermined target volume in a body with a particle beam. The apparatus comprises a device 84 for determination of an equivalent target volume and a device 86 for extending the equivalent target volume. The device 84 has an input 82 for receiving a data set which defines a minimum target volume. The input 82 is connected to a device 80 for formation of such a data set.

The device 80 is connected, for example, to a computed tomography device 71 or a nuclear spin tomography device for generation of tomographic images or to an X-ray device for (two-dimensional) fluoroscopy of the body to be irradiated. From one or more tomographic images, the device 80 generates, automatically or in dialogue with a medical technician, one or more data set(s) defining the minimum target volume or clinical target volume in one or more movement states. The data set(s) is/are transferred by the device 80 to the input 82 of the device 84.

From the minimum target volume transferred to it, in the movement state or states, the device 84 forms one or more equivalent target volumes, for example as has been described hereinbefore with reference to FIGS. 14 and 15. The equivalent target volumes are transferred to the extending device 86.

The extending device 86 forms, where applicable, a union of sets of the equivalent target volumes, for example as has been shown hereinbefore by FIGS. 11 and 16. Alternatively or additionally, the device 86 extends the equivalent target volume or the union of sets, as has been shown by way of example hereinbefore by FIGS. 4, 5 and 17. The planning target volume so formed is transferred to a control device 88 for controlling an irradiation system as has been described hereinbefore with reference to FIG. 1.

The control device 88 so controls the system that the latter directs a particle beam at all the target points located within the planning target volume in succession, in order to produce a therapeutically effective dose there.

The connections shown in FIG. 18 between the tomography device 71 and the devices 80, 84, 86 and the control device 88 are, in each case, connections in the form of electrical lines or glass fibre cables, but can also comprise data connections via the Internet or some other network or wireless data connections. In contrast to the above illustration in FIG. 18, the devices 80, 84, 86 can furthermore be integrated into a single device or single system, for example into an irradiation planning system.

Figure 19:
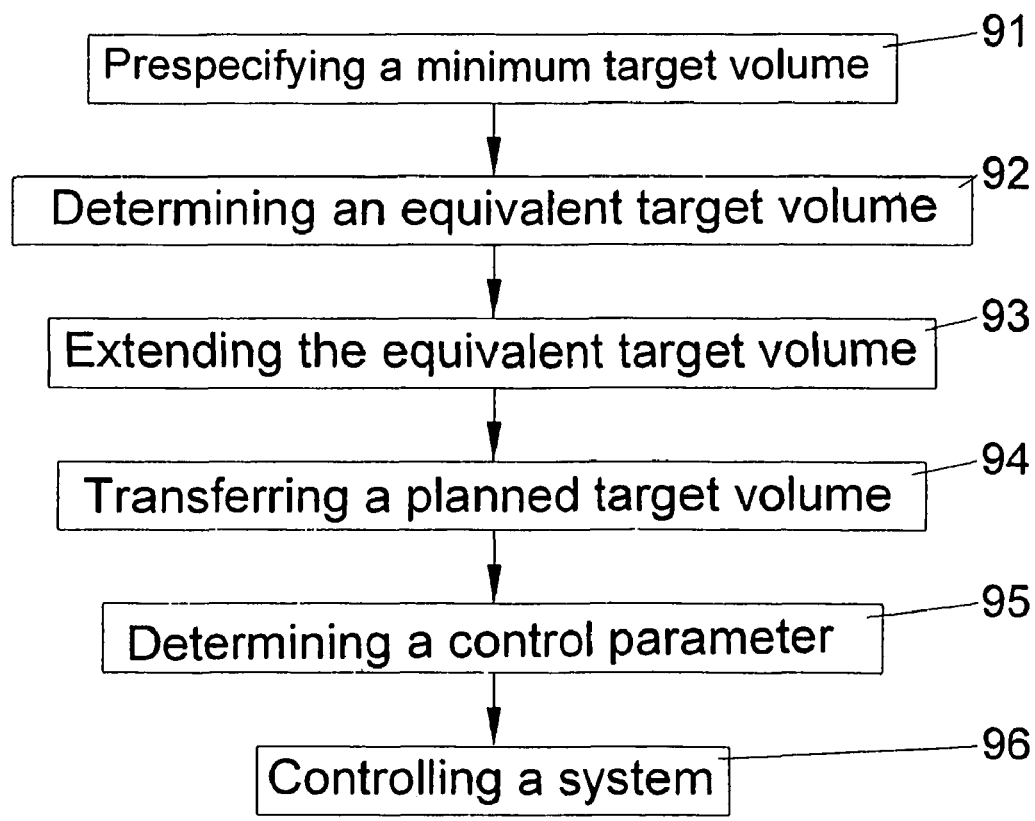
FIG. 19 shows, in diagrammatic form, a flow diagram of a method for determination of a planning target volume for a particle therapy system.

The devices 84 and 86 can be constructed in order to control or carry out a method as shown hereinbelow with reference to FIG. 19.

In a first step 91, a minimum target volume, for example the volume of a tumour or some other clinical target volume, is prespecified, for example in or by means of the device 80 shown hereinbefore by FIG. 18. In a second step 92, an equivalent target volume is determined from the minimum target volume, for example in the device 84 and for example in the manner shown hereinbefore by FIGS. 3, 9, 10, 14 and 15. In a third step 93, the equivalent target volume is extended, for example in the device 86 and for example in the manner shown hereinbefore by FIGS. 4, 5, 11, 16 and 17.

In a fourth step 94, the extended target volume is transferred as a planning target volume to a device which, in a fifth step 95, forms therefrom control parameters for controlling an irradiation system. The fifth step 95 can consist of a plurality of sub-steps which are carried out in a single device or in a plurality of devices coupled to one another. For example, from the planning target volume there can first be produced a data set containing the locations (co-ordinates perpendicular to the beam direction), particle energies, beam cross-sections and particle counts for all the target points. From that data set there are then determined the control parameters, which form a further data set.

The control parameters are transferred to a control device as has been shown, for example, hereinbefore by FIG. 18. In a sixth step 96, this device controls a system, as has been shown, by way of example, hereinbefore by FIG. 1, for irradiating a planning target volume.

If the target volume is to be irradiated several times from different directions, at least the above-described steps 92 to 96 are repeated for each direction. If the target volume is to be repeatedly irradiated from the same direction with time intervals (a plurality of irradiations or fractions in one irradiation programme), the above-described steps 91 to 95 can be carried out only once. When the steps are carried out once in this manner, the planning target volume and the control parameters are determined for all the irradiations or fractions in the irradiation programme. Only the sixth step 96 is repeated on each irradiation or fraction. Alternatively, steps 91 to 96 are carried out anew before or on each irradiation or fraction in order to modify the planning target volume and the control parameters in the event of a change in the clinical target volume.

The above-described steps can be carried out in a plurality of separate methods and at different points in time. For example, the first step 91, the second step 92 and the third step 93 are carried out immediately before the irradiation or also even some days or weeks beforehand in a first method. The fourth step 94, the fifth step 95 and the sixth step 96 can be carried out in one or more methods immediately after one another or spaced apart in time.

The exemplary embodiments described are suitable not only for use in the context of particle therapy. In addition, they can be used generally in systems for the irradiation of material, especially when the applied beam dose should vary spatially, and especially when the material has a non-homogeneous density and moves relative to the reference system of the system or is moved relative to the reference system of the system.

List Of Reference Numerals
10 particle therapy system
11 particle source
12 switching magnet
13 pre-accelerator
15 accelerator
17 high-energy beam transport system
19 irradiation room
20 particle beam
21 gantry
22 axis of gantry 21
23 body
24 equivalent body
25 target volume
26 equivalent target volume
27 further equivalent target volume
28 extended equivalent target volume or union of sets
29 planning target volume
30 target point
31 convolution kernel for lateral safety margin
32 convolution kernel for longitudinal safety margin
33 convolution kernel for longitudinal and lateral safety margin
34 convolution kernel for extended safety margin
40 cavity
41 region of unitary energy loss
42 region of double energy loss
45 minimum target volume
46 equivalent target volume
47 union of sets of the equivalent target volumes 46
51 target point in the lateral safety margin
52 target point in the longitudinal safety margin
53 target point both in the lateral and also in the longitudinal safety margin
55 target point in the lateral or longitudinal safety margin
58 target point in the extended safety margin
71 tomography device
80 device for formation of a data set
82 input for receiving the data set
84 device for determination of an equivalent target volume
86 device for extending the equivalent target volume
88 control device
91 first step
92 second step
93 third step
94 fourth step
95 fifth step
96 sixth step

The invention claimed is:

1. Method of determining a planning target volume for a system for irradiating a predetermined minimum target volume in a body with a particle beam, the system being constructed to direct the particle beam at a multiplicity of target points in the body in succession in order to produce at each of the target points a predetermined dose distribution, comprising the following steps:
   determining, in a fictive homogeneous body, a target volume equivalent to the minimum target volume in the body;
   extending the equivalent target volume by a safety margin, in order to determine the planning target volume.

2. Method according to claim 1, wherein the fictive homogeneous body is a body of water.

3. Method according to claim 1, wherein a width of the safety margin is matched to an inaccuracy of the position of the minimum target volume in a co-ordinate system of the irradiation system.

4. Method according to claim 1, wherein a width of the safety margin is matched to an inaccuracy of the composition of the body.

5. Method according to claim 1, wherein a width of the safety margin is matched to a possible change in the body during the irradiation or between a plurality of irradiations in an irradiation programme for protracted irradiation.

6. Method according to claim 1, wherein a width of the safety margin is matched to possible growth of the minimum target volume during the irradiation or between a plurality of irradiations in an irradiation programme for protracted irradiation.

7. Method according to claim 1, wherein a width of the safety margin is matched to possible movement of the minimum target volume of the body or of regions located in front of the minimum target volume in the beam direction during the irradiation or between a plurality of irradiations in an irradiation programme for protracted irradiation.

8. Method according to claim 1, wherein the safety margin has a predetermined fixed width at each location.

9. Method according to claim 1, further comprising the following step:
determining, in the fictive homogeneous body, a further equivalent target volume equivalent to the minimum target volume in the body in a further movement state,
wherein in the extending step the planning target volume is so determined that it includes the equivalent target volume and the further equivalent target volume.

10. Method according to claim 9, wherein the planning target volume includes the equivalent target volume, a safety margin around the equivalent target volume, the further equivalent target volume and a safety margin around the further equivalent target volume.

11. Method according to claim 1, wherein the planning target volume is determined by convolution of the equivalent target volume using a convolution kernel.

12. Method according to claim 1, wherein a three-dimensional raster of regions is placed over the body, and wherein the minimum target volume, the equivalent target volume, the safety margin and the planning target volume are in each case represented by a set of regions or target points.

13. Method according to claim 12, wherein the safety margin has, in each isoenergy layer, an extent of one or more target points.

14. Method according to claim 12, wherein the safety margin parallel to the direction of the particle beam has an extent of one or more target points.

15. Apparatus for determination of a planning target volume for a system for irradiating a predetermined minimum target volume in a body with a particle beam, the system being constructed to direct the particle beam at a multiplicity of target points in the body in succession, in order to produce at each of the target points a predetermined dose distribution, having:
a device for receiving a data set defining the minimum target volume;
a device, connected to the device for receiving, for determining, in a fictive homogeneous body, a target volume equivalent to the minimum target volume in the body;
a device for extending the equivalent target volume by a safety margin, in order to determine the planning target volume.

16. Apparatus according to claim 15, wherein the device for extending takes into account an inaccuracy of the position of the minimum target volume.

17. Apparatus according claim 15, wherein the device for extending takes into account an inaccuracy of the composition of the body.

18. Apparatus according to claim 15, wherein the device for extending takes into account a possible change in the body during the irradiation.

19. Apparatus according to claim 15, wherein the device for extending takes into account possible growth of the minimum target volume during the irradiation.

20. Apparatus according to claim 15, wherein the device for extending takes into account possible movement of the minimum target volume of the body during an irradiation or between a plurality of irradiations in an irradiation programme for protracted irradiation.

21. Apparatus according to claim 15, wherein
the device for receiving is constructed to receive a further data set which defines a further position of the minimum target volume;
the device for determination is constructed to determine a further equivalent target volume which is equivalent to the minimum target volume in the further position in the fictive homogeneous body;
the device for extending is constructed to determine the planning target volume so that it includes the equivalent target volume and the further equivalent target volume.

22. Apparatus according to claim 15, wherein the device for extending is constructed to determine the planning target volume by convolution of the equivalent target volume using a convolution kernel.

23. Apparatus according to claim 15, wherein the apparatus is a therapy planning apparatus.

24. System for irradiating a predetermined minimum target volume in a body with a particle beam, the system directing the particle beam at a multiplicity of target points in the body in succession in order to produce at each of the target points a predetermined dose distribution, and wherein the system comprises an apparatus according to claim 15.

* * * * *